("12") United States Patent  
Röben et al.

(10) Patent No.: US 9,388,200 B2  
(45) Date of Patent: Jul. 12, 2016

(54) UREA-CONTAINING MERCAPTOSILANES, PROCESS FOR PREPARATION THEREOF AND USE THEREOF

(71) Applicant: Evonik Industries AG, Essen (DE)

(72) Inventors: Caren Röben, Köln (DE); Ralph Moser, Freiburg i. Br. (DE); Stefanie Mayer, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/711,486

(22) Filed: May 13, 2015

(65) Prior Publication Data

US 2015/0329569 A1    Nov. 19, 2015

(30) Foreign Application Priority Data

May 15, 2014  (DE) .......................... 10 2014 209 233

(51) Int. Cl.  
*C07F 7/10* (2006.01)  
*C07F 7/18* (2006.01)

(52) U.S. Cl.  
CPC ............. *C07F 7/1804* (2013.01); *C07F 7/1836* (2013.01); *C07F 7/1872* (2013.01)

(58) Field of Classification Search  
CPC .................................... C07F 7/10; C07F 7/18  
USPC ....................................................... 556/421  
See application file for complete search history.

(56) References Cited

U.S. PATENT DOCUMENTS

| | | | |
|---|---|---|---|
| 2,509,483 A | 5/1950 | Crouch | |
| 3,637,789 A | 1/1972 | Legendre | |
| 3,946,059 A | 3/1976 | Janssen et al. | |
| 6,375,789 B1 * | 4/2002 | Katz | C08G 18/289 156/329 |
| 2003/0191270 A1 | 10/2003 | Musa | |
| 2009/0075096 A1 | 3/2009 | Butikofer | |

FOREIGN PATENT DOCUMENTS

| | | |
|---|---|---|
| DE | 3424534 | 1/1986 |
| DE | 10351735 | 12/2004 |
| DE | 60018483 | 1/2006 |
| EP | 1156053 | 11/2001 |
| EP | 1700861 | 9/2006 |
| EP | 2570419 | 3/2013 |
| JP | S59144792 | 8/1984 |
| JP | 2002201312 | 7/2002 |
| JP | 2002311574 | 10/2002 |
| JP | 2008279736 | 11/2008 |
| WO | 99/55754 | 11/1999 |
| WO | 2013/087698 | 6/2013 |

OTHER PUBLICATIONS

European Patent Office Search Report for Application No. 15161560.6 dated Oct. 7, 2015 (6 pages).
European Patent Office Search Report for Application No. 15161573.9 dated Oct. 2, 2015 (7 pages).
European Patent Office Search Report for Application No. 15161605.9 dated Oct. 6, 2015 (8 pages).
Xu et al., "A new strategy to prepare glutathione responsive silica nanoparticles," RSC Advances, 2013, 3, p. 17700.
Gudima, N. V. et al., "Sorption of gold and palladium on silica gel modified by N-(4-mercaptophenyl)-N'-propylurea groups," Ukrainskii Khimicheskii Zhurnal (Russian Edition), 2010, 76, pp. 114-118.
Mane et al., "An efficient and greener protocol towards synthesis of unsymetrical N,N'-biphenyl urea," Arabian Journal of Chemistry, 2011, 6, pp. 423-427.
United States Patent Office Notice of Allowance for U.S. Appl. No. 14/711,478 dated Sep. 25, 2015 (5 pages).
Wang et al., Database Accession No. 2014:1102076 (2014).
German Search Report for Application No. 15165590.9 dated Oct. 23, 2015 (9 pages).
Besson et al., "Soft route for monodisperse gold nanoparticles confined within SH-functionalized walls of mesoporous silica," J. Mat. Chem., 2009, 19, pp. 4746-4752.
German Search report for Application No. 102014209215.9 dated Jul. 31, 2014 (6 pages).
German Search report for Application No. 102014209221.3 dated Jul. 31, 2014 (5 pages).

(Continued)

*Primary Examiner* — Porfirio Nazario Gonzalez  
*Assistant Examiner* — Kofi Adzamli  
(74) *Attorney, Agent, or Firm* — Michael Best & Friedrich LLP

(57) ABSTRACT

The invention relates to urea-containing mercaptosilanes of the formula I

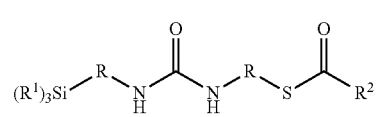

which are prepared by reacting a halosilane of the formula II

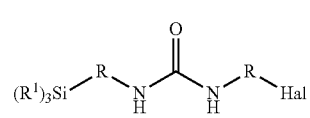

with compounds of the formula III

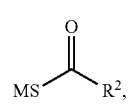

in an alcohol.

13 Claims, No Drawings

(56) References Cited

OTHER PUBLICATIONS

German Search Report for Application No. 102014209226.4 dated Aug. 5, 2014 (6 pages).
German Search Report for Application No. 102014209239.6 dated Oct. 8, 2014 (6 pages).
Harpp et al., "Organic Sulfur Chemistry. X. Selective Desulfurization of Disulfides. Scope and Mechanism," Organic Sulfur Chemistry, 1970, pp. 2437-2443.
Wang et al, "Fabrication of Single-Hole Glutathione-Responsive Degradable Hollow Silica Nanoparticles for Drug Delivery," Applied Materials and Interfaces, American Chemical Society, 2014, 6, pp. 12600-12608.
United States Patent Office Notice of Allowance for U.S. Appl. No. 14/711,478 dated Jul. 17, 2015 (8 pages).
German Search Report for Application No. 102014209233.7 dated Oct. 13, 2014 (6 pages).
European Patent Office Search Report for Application No. 15165635.2 dated Sep. 17, 2015 (3 pages).
United States Patent Office Notice of Allowance for U.S. Appl. No. 14/711,468 dated May 13, 2016 (12 pages).
United States Patent Office Notice of Allowance for U.S. Appl. No. 14/711,463 dated May 20, 2016 (11 pages).
United States Patent Office Action for U.S. Appl. No. 14/711,473 dated May 11, 2016 (8 pages).

\* cited by examiner

UREA-CONTAINING MERCAPTOSILANES, PROCESS FOR PREPARATION THEREOF AND USE THEREOF

CROSS-REFERENCE TO RELATED APPLICATIONS

This patent application claims the benefit of priority to German Application No. 102014209233.7, filed on May 15, 2014, the disclosure of which is incorporated by reference herein in its entirety, and priority to which is hereby claimed.

The invention relates to urea-containing mercaptosilanes, to processes for preparation thereof and to the use thereof.

CAS 1082204-82-7, 1268617-33-9 and 104261-54-3 disclose compounds of the formula

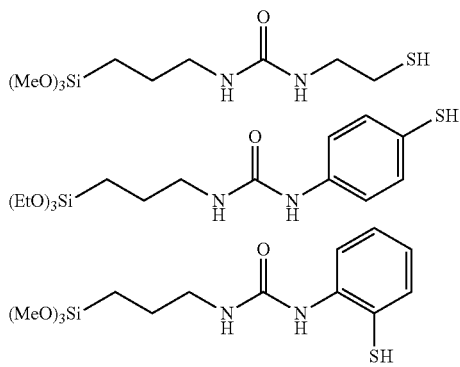

In addition, JP 2008279736 A discloses urea-containing silanes for coatings.

DE 3424534 A1 discloses N,N'- and N,N',N'-substituted urea-containing silanes of the formula

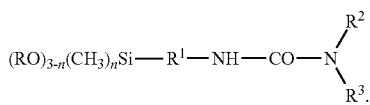

The preparation is effected by reacting an amino compound, a halosilane and alkali metal cyanate in an aprotic polar organic solvent, for example DMF or DMSO.

In addition, JP 2002311574 discloses powder coatings comprising silanes of the formula

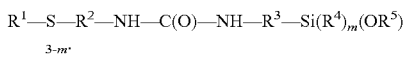

WO 9955754 A1 discloses photosensitive resin compositions comprising alkoxysilanes of the formula

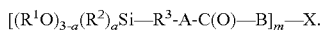

Disadvantages of the known urea-containing mercaptosilanes are poor processing characteristics, low network density, poor wet skid properties and low dynamic stiffness.

It is an object of the present invention to provide urea-containing mercaptosilanes having improved processing characteristics, network density, wet skid properties and dynamic stiffness in rubber mixtures compared to urea-containing mercaptosilanes known from the prior art.

The invention provides a urea-containing mercaptosilane of the formula I

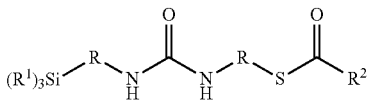

where $R^1$ are the same or different and are C1-C10 alkoxy groups, preferably methoxy or ethoxy group, C2-C10 cyclic dialkoxy groups, phenoxy group, C4-C10 cycloalkoxy groups, C6-C20 aryl groups, preferably phenyl, C1-C10 alkyl groups, preferably methyl or ethyl, C2-C20 alkenyl group, C7-C20 aralkyl group or halogen, preferably Cl, $R^2$ is a monovalent C1-C20 hydrocarbon group, preferably a C1-C20 alkyl group, C6-C20 aryl group, C2-C20 alkenyl group or C7-C20 aralkyl group, and R are the same or different and are a branched or unbranched, saturated or unsaturated, aliphatic, aromatic or mixed aliphatic/aromatic divalent $C_1$-$C_{30}$, preferably $C_1$-$C_{20}$, more preferably $C_1$-$C_{10}$, even more preferably $C_1$-$C_7$, especially preferably $C_2$ and $C_3$, hydrocarbon group optionally substituted by F—, Cl—, Br—, I—, —CN or HS—.

Urea-containing mercaptosilanes may be mixtures of urea-containing mercaptosilanes of the formula I.

The process product may comprise oligomers which form through hydrolysis and condensation of the alkoxysilane functions of the urea-containing mercaptosilanes of the formula I.

The urea-containing mercaptosilanes of the formula I may be applied to a support, for example wax, polymer or carbon black. The urea-containing mercaptosilanes of the formula I may be applied to a silica, in which case the binding may be physical or chemical.

R may preferably be

—CH$_2$—, —CH$_2$CH$_2$—, —CH$_2$CH$_2$CH$_2$—, —CH$_2$CH$_2$CH$_2$CH$_2$—, —CH(CH$_3$)—, —CH$_2$CH(CH$_3$)—, —CH(CH$_3$)CH$_2$—, —C(CH$_3$)$_2$—, —CH(C$_2$H$_5$)—, —CH$_2$CH$_2$CH(CH$_3$)—, —CH(CH$_3$)CH$_2$CH$_2$—,

—CH$_2$CH(CH$_3$)CH$_2$—, —CH$_2$CH$_2$CH$_2$CH$_2$CH$_2$—, —CH$_2$CH$_2$CH$_2$CH$_2$CH$_2$CH$_2$—,

—CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$CH$_2$CH$_2$CH$_2$CH$_2$— or

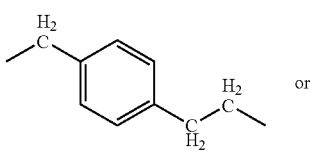

-continued

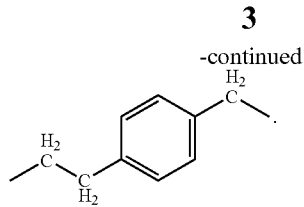

$R^1$ may preferably be methoxy or ethoxy.

$R^2$ may preferably be $CH_3$, $CH_2CH_3$, $CH_2CH_2CH_3$ oder $(CH_2)_6CH_3$.

Urea-containing mercaptosilanes of the formula I may preferably be:

(CH$_3$CH$_2$O)$_3$Si—CH$_2$—NH—CO—NH—CH$_2$—S—C(O)—CH$_3$,
(CH$_3$CH$_2$O)$_3$Si—CH$_2$CH$_2$—NH—CO—NH—CH$_2$—S—C(O)—CH$_3$,
(CH$_3$CH$_2$O)$_3$Si—CH$_2$—NH—CO—NH—CH$_2$CH$_2$—S—C(O)—CH$_3$,
(CH$_3$CH$_2$O)$_3$Si—CH$_2$CH$_2$—NH—CO—NH—CH$_2$CH$_2$—S—C(O)—CH$_3$,
(CH$_3$CH$_2$O)$_3$Si—CH$_2$CH$_2$CH$_2$—NH—CO—NH—CH$_2$—S—C(O)—CH$_3$,
(CH$_3$CH$_2$O)$_3$Si—CH$_2$CH$_2$CH$_2$—NH—CO—NH—CH$_2$CH$_2$—S—C(O)—CH$_3$,
(CH$_3$CH$_2$O)$_3$Si—CH$_2$—NH—CO—NH—CH$_2$CH$_2$CH$_2$—S—C(O)—CH$_3$,
(CH$_3$CH$_2$O)$_3$Si—CH$_2$CH$_2$—NH—CO—NH—CH$_2$CH$_2$CH$_2$—S—C(O)—CH$_3$,
(CH$_3$CH$_2$O)$_3$Si—CH$_2$CH$_2$CH$_2$—NH—CO—NH—CH$_2$CH$_2$CH$_2$—S—C(O)—CH$_3$,
(CH$_3$CH$_2$O)$_3$Si—CH$_2$—NH—CO—NH—CH$_2$—S—C(O)—(CH$_2$)$_6$CH$_3$,
(CH$_3$CH$_2$O)$_3$Si—CH$_2$CH$_2$—NH—CO—NH—CH$_2$—S—C(O)—(CH$_2$)$_6$CH$_3$,
(CH$_3$CH$_2$O)$_3$Si—CH$_2$—NH—CO—NH—CH$_2$CH$_2$—S—C(O)—(CH$_2$)$_6$CH$_3$,
(CH$_3$CH$_2$O)$_3$Si—CH$_2$CH$_2$—NH—CO—NH—CH$_2$CH$_2$—S—C(O)—(CH$_2$)$_6$CH$_3$,
(CH$_3$CH$_2$O)$_3$Si—CH$_2$CH$_2$CH$_2$—NH—CO—NH—CH$_2$—S—C(O)—(CH$_2$)$_6$CH$_3$,
(CH$_3$CH$_2$O)$_3$Si—CH$_2$CH$_2$CH$_2$—NH—CO—NH—CH$_2$CH$_2$—S—C(O)—(CH$_2$)$_6$CH$_3$,
(CH$_3$CH$_2$O)$_3$Si—CH$_2$—NH—CO—NH—CH$_2$CH$_2$CH$_2$—S—C(O)—(CH$_2$)$_6$CH$_3$,
(CH$_3$CH$_2$O)$_3$Si—CH$_2$CH$_2$—NH—CO—NH—CH$_2$CH$_2$CH$_2$—S—C(O)—(CH$_2$)$_6$CH$_3$,
(CH$_3$CH$_2$O)$_3$Si—CH$_2$CH$_2$CH$_2$—NH—CO—NH—CH$_2$CH$_2$CH$_2$—S—C(O)—(CH$_2$)$_6$CH$_3$,
(CH$_3$O)$_3$Si—CH$_2$—NH—CO—NH—CH$_2$—S—C(O)—CH$_3$,
(CH$_3$O)$_3$Si—CH$_2$CH$_2$—NH—CO—NH—CH$_2$—S—C(O)—CH$_3$,
(CH$_3$O)$_3$Si—CH$_2$—NH—CO—NH—CH$_2$CH$_2$—S—C(O)—CH$_3$,
(CH$_3$O)$_3$Si—CH$_2$CH$_2$—NH—CO—NH—CH$_2$CH$_2$—S—C(O)—CH$_3$,
(CH$_3$O)$_3$Si—CH$_2$CH$_2$CH$_2$—NH—CO—NH—CH$_2$—S—C(O)—CH$_3$,
(CH$_3$O)$_3$Si—CH$_2$CH$_2$CH$_2$—NH—CO—NH—CH$_2$CH$_2$—S—C(O)—CH$_3$,
(CH$_3$O)$_3$Si—CH$_2$—NH—CO—NH—CH$_2$CH$_2$CH$_2$—S—C(O)—CH$_3$,
(CH$_3$O)$_3$Si—CH$_2$CH$_2$—NH—CO—NH—CH$_2$CH$_2$CH$_2$—S—C(O)—CH$_3$,
(CH$_3$O)$_3$Si—CH$_2$CH$_2$CH$_2$—NH—CO—NH—CH$_2$CH$_2$CH$_2$—S—C(O)—CH$_3$,
(CH$_3$O)$_3$Si—CH$_2$—NH—CO—NH—CH$_2$—S—C(O)—(CH$_2$)$_6$CH$_3$,
(CH$_3$O)$_3$Si—CH$_2$CH$_2$—NH—CO—NH—CH$_2$—S—C(O)—(CH$_2$)$_6$CH$_3$,
(CH$_3$O)$_3$Si—CH$_2$—NH—CO—NH—CH$_2$CH$_2$—S—C(O)—(CH$_2$)$_6$CH$_3$,
(CH$_3$O)$_3$Si—CH$_2$CH$_2$—NH—CO—NH—CH$_2$CH$_2$—S—C(O)—(CH$_2$)$_6$CH$_3$,
(CH$_3$O)$_3$Si—CH$_2$CH$_2$CH$_2$—NH—CO—NH—CH$_2$—S—C(O)—(CH$_2$)$_6$CH$_3$,
(CH$_3$O)$_3$Si—CH$_2$CH$_2$CH$_2$—NH—CO—NH—CH$_2$CH$_2$—S—C(O)—(CH$_2$)$_6$CH$_3$,
(CH$_3$O)$_3$Si—CH$_2$—NH—CO—NH—CH$_2$CH$_2$CH$_2$—S—C(O)—(CH$_2$)$_6$CH$_3$,
(CH$_3$O)$_3$Si—CH$_2$CH$_2$—NH—CO—NH—CH$_2$CH$_2$CH$_2$—S—C(O)—(CH$_2$)$_6$CH$_3$,
(CH$_3$O)$_3$Si—CH$_2$CH$_2$CH$_2$—NH—CO—NH—CH$_2$CH$_2$CH$_2$—S—C(O)—(CH$_2$)$_6$CH$_3$.

An especially preferred compound is of the formula (EtO)$_3$Si—CH$_2$CH$_2$CH$_2$—NH—CO—NH—CH$_2$CH$_2$—S—C(O)—CH$_3$.

The invention further provides a process for preparing the inventive urea-containing mercaptosilanes of the formula I

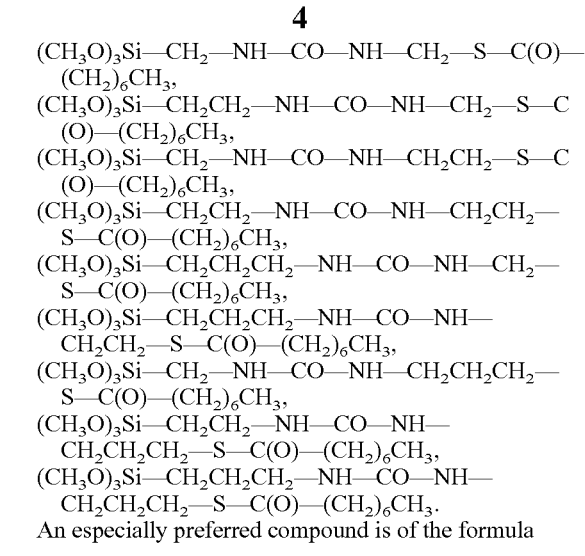

where $R^1$, $R^2$ and R are each as defined above, which is characterized in that a halosilane of the formula II

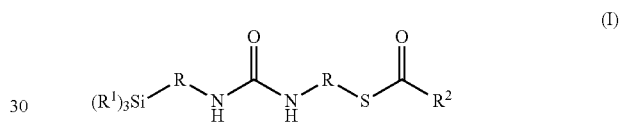

is reacted with a compound of formula III

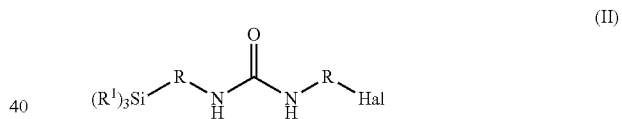

where $R^1$, $R^2$ and R are each as defined above, Hal is F, Cl, Br or I, preferably Cl, and M is an alkali metal, preferably K or Na, in an alcohol.

Halosilanes of the formula II may preferably be:

(C$_2$H$_5$O)$_3$Si—CH$_2$—NH—C(O)—NH—CH$_2$—Cl,
(C$_2$H$_5$O)$_3$Si—CH$_2$CH$_2$—NH—C(O)—NH—CH$_2$—Cl,
(C$_2$H$_5$O)$_3$Si—CH$_2$CH$_2$CH$_2$—NH—C(O)—NH—CH$_2$—Cl,
(C$_2$H$_5$O)$_3$Si—CH$_2$—NH—C(O)—NH—CH$_2$CH$_2$—Cl,
(C2H$_5$O)$_3$Si—CH$_2$CH$_2$—NH—C(O)—NH—CH$_2$CH$_2$—Cl,
(C$_2$H$_5$O)$_3$Si—CH$_2$—NH—C(O)—NH—CH$_2$CH$_2$—Cl,
(C$_2$H$_5$O)$_3$Si—CH$_2$—NH—C(O)—NH—CH$_2$CH$_2$CH$_2$—Cl,
(C$_2$H$_5$O)$_3$Si—CH$_2$CH$_2$—NH—C(O)—NH—CH$_2$CH$_2$CH$_2$—Cl, (C₂H₅O)₃Si—CH₂CH₂CH₂—NH—C(O)—NH—CH₂CH₂CH₂—Cl,
(CH₃O)₃Si—CH₂—NH—C(O)—NH—CH₂—Cl,
(CH₃O)₃Si—CH₂CH₂—NH—C(O)—NH—CH₂—Cl,
(CH₃O)₃Si—CH₂CH₂CH₂—NH—C(O)—NH—CH₂—Cl,
(CH₃O)₃Si—CH₂—NH—C(O)—NH—CH₂CH₂—Cl,
(CH₃O)₃Si—CH₂CH₂—NH—C(O)—NH—CH₂CH₂—Cl,
(CH₃O)₃Si—CH₂CH₂CH₂—NH—C(O)—NH—CH₂CH₂—Cl,
(CH₃O)₃Si—CH₂—NH—C(O)—NH—CH₂CH₂CH₂—Cl,
(CH₃O)₃Si—CH₂CH₂—NH—C(O)—NH—CH₂CH₂CH₂—Cl or
(CH₃O)₃Si—CH₂CH₂CH₂—NH—C(O)—NH—CH₂CH₂CH₂—Cl.

Compounds of the formula III may preferably be:
NaS—C(O)—CH₃,
NaS—C(O)—CH₂CH₃,
NaS—C(O)—CH₂CH₂CH₃,
NaS—C(O)—(CH₂)₆CH₃,
KS—C(O)—CH₃,
KS—C(O)—CH₂CH₃,
KS—C(O)—CH₂CH₂CH₃ or
KS—C(O)—(CH₂)₆CH₃.

In the process according to the invention, the halosilane of the formula II may be metered into the compound of the formula III.

In the process according to the invention, compound of the formula III may preferably be metered into halosilane of the formula II.

In the process according to the invention, the halosilane of the formula II can be used relative to the compound of the formula III in a molar ratio of 0.85:1 to 1.15:1, preferably 0.90:1 to 1.10:1, more preferably in a ratio of 0.95:1 to 1.05:1.

The reaction can be conducted with exclusion of air.

The reaction may be carried out under a protective gas atmosphere, for example under argon or nitrogen, preferably under nitrogen.

The process of the invention can be carried out at atmospheric pressure, elevated pressure or reduced pressure. Preferably, the process according to the invention can be conducted at standard pressure.

Elevated pressure may be a pressure from 1.1 bar to 100 bar, preferably of 1.5 bar to 50 bar, more preferably of 2 bar to 20 bar and very preferably of 2 to 10 bar.

Reduced pressure may be a pressure of 1 mbar to 1000 mbar, preferably 1 mbar to 500 mbar, more preferably 1 mbar to 250 mbar, very preferably 5 mbar to 100 mbar.

The process according to the invention can be conducted between 0° C. and 150° C., preferably between 20° C. and 100° C., more preferably between 50° C. and 80° C. Especially preferably, the process according to the invention can be conducted at the boiling point of the alcohol.

The alcohol used in the process according to the invention may preferably be methanol, ethanol, propanol, butanol or cyclohexanol. The alcohol may especially preferably be ethanol.

The alcohol can be removed, preferably distilled off, after the reaction.

The reaction product can subsequently be dried. The drying can be effected at temperatures of +20° C.-+100° C., preferably of +25° C.-+75° C. The drying can be effected at a reduced pressure of 1-500 mbar.

The urea-containing mercaptosilane of the formula I obtainable by the process according to the invention

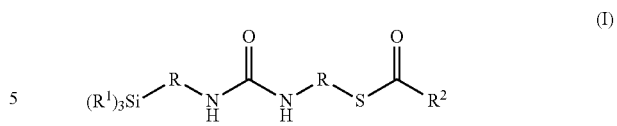

can be obtained in a yield of greater than 50%, preferably greater than 60%, very preferably greater than 70%.

In one embodiment, the halosilane of the formula II, prior to the reaction with the compound of the formula III, can be prepared from the hydrochloride salt of an amine of the formula IV

and isocyanatosilane of the formula V

by addition of a base, preferably NaOEt, where Hal, R¹ and R are each as defined above.

The base can be added until a pH between 7 and 14 is established.

In the process according to the invention, the hydrochloride salt of the amines of the formula IV can be used relative to isocyanatosilane of the formula V in a molar ratio of 0.85:1 to 1.15:1, preferably 0.90:1 to 1.10:1, more preferably in a ratio of 0.95:1 to 1.05:1.

In the aforementioned embodiment, the process according to the invention for preparing urea-containing mercaptosilanes of the formula I

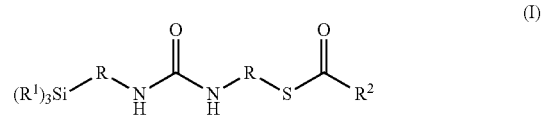

where R¹, R² and R are each as defined above may be characterized in that the hydrochloride salt of the amine of the formula IV

is dissolved in alcohol and reacted with a base, then the isocyanatosilane of the formula V

is added, and then compounds of the formula III

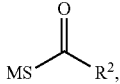
(III)

are added, the mixture is filtered and the solvent is removed, where Hal, M, $R^1$, $R^2$ and R are each as defined above.

In a further embodiment, the halosilane of the formula II, prior to the reaction with the compound of the formula III, can be prepared from the isocyanate-halogen compound of the formula VI

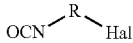
(VI)

and aminosilane of the formula VII

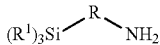
(VII)

where Hal, R and $R^1$ are each as defined above.

The reaction can be conducted in a solvent, preferably alcohol, more preferably ethanol.

In the process according to the invention, the isocyanate-halogen compound of the formula VI can be used relative to aminosilane of the formula VII in a molar ratio of 0.85:1 to 1.15:1, preferably 0.90:1 to 1.10:1, more preferably in a ratio of 0.95:1 to 1.05:1.

In the aforementioned embodiment, the process according to the invention for preparing urea-containing mercaptosilanes of the formula I

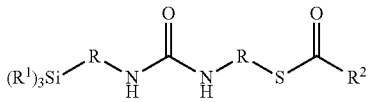
(I)

where $R^1$, $R^2$ and R are each as defined above may be characterized in that an isocyanate-halogen compound of the formula VI

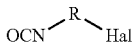
(VI)

and aminosilane of the formula VII

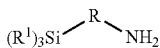
(VII)

are reacted in alcohol, preferably ethanol, and then a compound of the formula III

(III)

is added, the mixture is filtered and the alcohol is removed, where Hal, M, R, $R^1$ and $R^2$ are each as defined above.

The product prepared by the process according to the invention may have a residual content of halosilane of the formula II of less than 25 mol %, preferably less than 10 mol %, more preferably less than 5 mol %, very preferably less than 3 mol %.

The relative molar percentages of the halosilane of the formula II in the product prepared by the process according to the invention are determined in the $^1$H NMR by integration of the hydrogen atoms in the —CH$_2$C$\underline{H}_2$—Cl group of the halosilane of the formula II against the hydrogen atoms in the Si—C$\underline{H}_2$— group of the urea-containing mercaptosilane of the formula I. For the substance of the formula II (EtO)$_3$Si—CH$_2$CH$_2$CH$_2$—NH—CO—NH—CH$_2$CH$_2$—Cl, for example, the integral of the hydrogen atoms of the —CH$_2$C$\underline{H}_2$—Cl group (δ=3.17 ppm) is used for the determination of the relative contents.

The product prepared by the process according to the invention may have a residual content of hydrochloride salt of an amine of the formula IV of less than 25 mol %, preferably less than 10 mol %, more preferably less than 5 mol %, very preferably less than 3 mol %.

The relative molar percentages of the hydrochloride salt of an amine of the formula IV in the product prepared by the process according to the invention are determined in the $^{13}$C NMR by integration of the carbon atoms in the —$\underline{C}$H$_2$—NH$_2$.HCl group of the hydrochloride salt of an amine of the formula IV against the carbon atoms in the Si—$\underline{C}$H$_2$— group of the urea-containing mercaptosilane of the formula I. For the substance of the formula IV HCl.H$_2$N—CH$_2$—CH$_2$—Cl, for example, the integral of the carbon atoms of the HCl.H$_2$N—$\underline{C}$H$_2$—CH$_2$—Cl group (δ=41.25 ppm) or of the HCl.H$_2$N—CH$_2$—$\underline{C}$H$_2$—Cl group (δ=40.79 ppm) is used for the determination of the relative contents.

The product prepared by the process according to the invention may have a residual content of isocyanatosilane of the formula V of less than 10 mol %, preferably less than 5 mol %, more preferably less than 1 mol %, very preferably less than 0.1 mol %.

The relative molar percentages of the isocyanatosilane of the formula V in the product within a range of >1 mol %, prepared by the process according to the invention, are determined in the $^{13}$C NMR by integration of the carbon atoms in the —N$\underline{C}$O group of the isocyanatosilane of the formula V against the carbon atoms in the Si—$\underline{C}$H$_2$— group of the urea-containing mercaptosilanes of the formula I. For the substance of the formula V (EtO)$_3$Si—CH$_2$—CH$_2$—CH$_2$—NCO, for example, the integral of the carbon atoms of the —N$\underline{C}$O group (δ122.22 ppm) is used for the determination of the relative contents within a range of >1 mol %.

The relative molar percentages of the isocyanatosilane of the formula V in the product within a range of <1 mol %, prepared by the process according to the invention, are determined by quantitative FT-IR spectroscopy known to those skilled in the art. The method is calibrated by using calibration solutions of suitable concentration (for example in C$_2$Cl$_4$). For the measurement, about 1 g sample is weighed into a 25 ml rollneck bottle, and 25 g of C$_2$Cl$_4$ are added. The sample is agitated on an agitator for 1-2 hours. Thereafter, the lower liquid phase is metered cautiously into a 20 mm IR cuvette and analysed by FT-IR spectroscopy (4000-1200 cm$^{-1}$, resolution 2 cm$^{-1}$). Under the same conditions, a spectrum of the solvent is recorded for subtraction.

For the substance of the formula V (EtO)$_3$Si—CH$_2$—CH$_2$—CH$_2$—NCO, for example, the wavelength of the valence vibration of the —NCO group at 2270 cm$^{-1}$ is used for the determination of the relative contents within a range of <1 mol %.

The product prepared by the process according to the invention may have a residual content of isocyanate-halogen compound of the formula VI of less than 25 mol %, preferably less than 10 mol %, more preferably less than 5 mol %, very preferably less than 3 mol %.

The relative molar percentages of the isocyanate-halogen compound of the formula VI in the product prepared by the process according to the invention are determined in the $^{13}$C NMR by integration of the carbon atoms in the OCN—CH$_2$— group of the isocyanate-halogen compound of the formula VI against the carbon atoms in the Si—CH$_2$— group of the urea-containing mercaptosilane of the formula I.
For the substance of the formula VI OCN—CH$_2$—CH$_2$—Cl, for example, the integral of the carbon atoms of the OCN—CH$_2$— group (δ=124.33 ppm) is used for the determination of the relative contents.

The product prepared by the process according to the invention may have a residual content of aminosilane of the formula VII of less than 10 mol %, preferably less than 5 mol %, more preferably less than 1 mol %, very preferably less than 0.1 mol %.

The relative molar percentages of the aminosilane of the formula VII in the product prepared by the process according to the invention are determined in the $^{13}$C NMR by integration of the carbon atoms in the —CH$_2$—NH$_2$ group of the aminosilane of the formula VII against the carbon atoms in the Si—CH$_2$— group of the urea-containing mercaptosilane of the formula I.

For the substance of the formula VII (EtO)$_3$Si—CH$_2$—CH$_2$—CH$_2$—NH$_2$, for example, the integral of the carbon atoms of the —CH$_2$—NH$_2$ group (δ=45.15 ppm) is used for the determination of the relative contents.

Urea-containing mercaptosilane of the formula I prepared by the process according to the invention can be characterized by a $^1$H, $^{13}$C or $^{29}$Si NMR method known to those skilled in the art.

The soluble fraction of the urea-containing mercaptosilane of the formula I in the products obtained by the processes according to the invention in DMSO-d$^6$ or CDCl$_3$ is determined by adding an internal standard, for example triphenylphosphine oxide (TPPO), in DMSO-d6 or in CDCl$_3$, and a $^1$H NMR method known to those skilled in the art.

The urea-containing mercaptosilanes of the formula I can be used as adhesion promoters between inorganic materials, for example
glass beads, glass shards, glass surfaces, glass fibres, or oxidic fillers, preferably silicas such as precipitated silicas and fumed silicas,
and organic polymers, for example thermosets, thermoplastics or elastomers, or as crosslinking agents and surface modifiers for oxidic surfaces.

The urea-containing mercaptosilanes of the formula I may be used as coupling reagents in filled rubber mixtures, examples being tyre treads, industrial rubber articles or footwear soles.

Advantages of the inventive urea-containing mercaptosilanes of the formula I are improved processing characteristics, network density, wet skid properties and dynamic stiffness in rubber mixtures.

EXAMPLES

Comparative Example 1

Preparation of (EtO)$_3$Si—CH$_2$CH$_2$CH$_2$—NH—CO—NH—CH$_2$CH$_2$—SH from (EtO)$_3$Si—CH$_2$CH$_2$CH$_2$—NH—CO—NH—CH$_2$CH$_2$—Cl and NaSH To a solution of NaSH in ethanol [prepared by introducing H$_2$S (15.21 g, 0.45 mol, 1.07 eq) into a sodium ethoxide solution (prepared from Na (10.55 g, 0.46 mol, 1.10 eq) in EtOH (300 mL))] is added, by metered addition at 52° C., (EtO)$_3$Si—CH$_2$CH$_2$CH$_2$—NH—CO—NH—CH$_2$CH$_2$—Cl (138.90 g, 0.42 mol, 1.00 eq) in ethanol (300 ml), and the mixture is heated to 78° C. After a reaction time of 5 h, the mixture is cooled to room temperature and the suspension is filtered. The filtrate is freed of the solvent on a rotary evaporator and dried under reduced pressure. The (EtO)$_3$Si—CH$_2$CH$_2$CH$_2$—NH—CO—NH—CH$_2$CH$_2$—SH product (134.96 g, 97.9% of theory) is obtained as a white solid.
$^1$H NMR (δ$_{ppm}$, 500 MHz, CDCl$_3$): 0.64 (2H, t), 1.23 (9H, t), 1.36 (1H, br), 1.61 (2H, m), 2.67 (2H, t), 3.17 (2H, m), 3.37 (2H, m), 3.81 (6H, q), 4.74 (1H, br), 4.94 (1H, br); $^{13}$C NMR (δ$_{ppm}$, 125 MHz, CDCl$_3$): 7.8 (1C), 18.3 (3C), 23.8 (1C), 25.6 (1C), 43.0 (1C), 43.5 (1C), 58.4 (3C), 158.9 (1C).

Example 1

Preparation of (EtO)$_3$Si—CH$_2$CH$_2$CH$_2$—NH—CO—NH—CH$_2$CH$_2$—S—CO—CH$_3$ from (EtO)$_3$Si—CH$_2$CH$_2$CH$_2$—NH—CO—NH—CH$_2$CH$_2$—Cl and KSAc (EtO)$_3$Si—CH$_2$CH$_2$CH$_2$—NH—CO—NH—CH$_2$CH$_2$—Cl (81.52 g, 0.25 mol, 1.00 eq) is initially charged in ethanol (85 ml) in a 500 ml three-neck flask with stirrer, reflux condenser and internal thermometer. Potassium thioacetate (28.48 g, 0.25 mol, 1.00 eq) is added and the mixture is heated to reflux. After a reaction time of 3.5 h, the mixture is cooled to room temperature and the suspension is filtered. The filtrate is freed of the solvent on a rotary evaporator and dried under reduced pressure. The (EtO)$_3$Si—CH$_2$CH$_2$CH$_2$—NH—CO—NH—CH$_2$CH$_2$—S—CH$_3$ product (81.64 g, 89% of theory) is obtained as a light brown solid.
$^1$H NMR (δ$_{ppm}$, 500 MHz, CDCl$_3$): 0.64 (2H, t), 1.24 (9H, t), 1.61 (2H, m), 2.35 (3H, s), 3.01 (2H, t), 3.16 (2H, t), 3.34 (2H, t), 3.82 (6H, q), 4.5-7.0 (2H, br); $^{13}$C NMR (δ$_{ppm}$, 125 MHz, CDCl$_3$): 7.8 (1C), 18.3 (3C), 23.8 (1C), 29.9 (1C), 30.6 (1C), 40.0 (1C), 43.0 (1C), 58.4 (3C), 159.0 (1C), 195.8 (1C).

Example 2

Preparation of (EtO)$_3$Si—CH$_2$CH$_2$CH$_2$—NH—CO—NH—CH$_2$CH$_2$—S—CO—CH$_3$ from (EtO)$_3$Si—CH$_2$CH$_2$CH$_2$—NH$_2$, OCN—CH$_2$CH$_2$—Cl and KSAc 3-Aminopropyltriethoxysilane (132.82 g, 0.60 mol, 1.00 eq) is initially charged in ethanol (300 ml) in a three-neck flask with precision glass stirrer, internal thermometer, dropping funnel and reflux condenser, and cooled to −78° C.

2-Chloroethyl isocyanate (63.34 g, 0.60 mol, 1.00 eq) is added dropwise at −78 to −68° C. within 1.75 h and then the mixture is heated to 50° C. Potassium thioacetate (68.53 g, 0.60 mol, 1.00 eq) is added in five portions and the mixture is heated to reflux. After a reaction time of 2.25 h, the mixture is cooled to room temperature and the suspension is filtered. The filtrate is freed of the solvent on a rotary evaporator and dried under reduced pressure. The (EtO)$_3$Si—CH$_2$CH$_2$CH$_2$—NH—CO—NH—CH$_2$CH$_2$—S—CH$_3$ product (213.91 g, 97.3% of theory) is obtained as a waxy white solid.

$^1$H NMR ($\delta_{ppm}$, 500 MHz, CDCl$_3$): 0.64 (2H, t), 1.22 (9H, t), 1.62 (2H, m), 2.35 (3H, s), 3.01 (2H, t), 3.16 (2H, t), 3.34 (2H, t), 3.82 (6H, q), 4.7-5.0 (2H, br); $^{13}$C NMR ($\delta_{ppm}$, 125 MHz, CDCl$_3$): 7.8 (1C), 18.3 (3C), 23.8 (1C), 29.9 (1C), 30.6 (1C), 40.1 (1C), 43.0 (1C), 58.4 (3C), 158.7 (1C), 195.9 (1C).

Example 3

Preparation of (EtO)$_3$Si—CH$_2$CH$_2$CH$_2$—NH—CO—NH—CH$_2$CH$_2$—S—CH$_3$ from (EtO)$_3$Si—CH$_2$CH$_2$CH$_2$—NCO, HCl·H$_2$N—CH$_2$CH$_2$—Cl and KSAc 2-Chloroethylamine hydrochloride (73.86 g, 0.70 mol, 1.00 eq) is initially charged in ethanol (2.0 l) in a 4 l three-neck flask with precision glass stirrer, internal thermometer, dropping funnel and reflux condenser, and cooled to −78° C., and sodium ethoxide (226.83 g, 0.70 mol, 1.00 eq, 21% in ethanol) is added. 3-Isocyanatopropyl(triethoxysilane) (173.15 g, 0.70 mol, 1.00 eq) is then added dropwise at −78 to −65° C. within 3 h and then the mixture is heated to 50° C. Potassium thioacetate (79.95 g, 0.70 mol, 1.00 eq) is added in five portions and the mixture is heated to reflux. After a reaction time of 4 h, the mixture is cooled to room temperature and the suspension is filtered. The filtrate is freed of the solvent on a rotary evaporator and dried under reduced pressure. The (EtO)$_3$Si—CH$_2$CH$_2$CH$_2$—NH—CO—NH—CH$_2$CH$_2$—S—CH$_2$CH$_3$ product (288.02 g, quant.) is obtained as an orange oil.

Example 4

Rubber Mixtures

The formulation used for the rubber mixtures is specified in Table 1 below. In this table, the unit phr means parts by weight based on 100 parts by weight of the raw rubber used. The inventive silane is used in isomolar amounts relative to the comparative silane.

TABLE 1

| Substance | Amount [phr] Ref. rubber mixture I comprising Comp. Ex. 1 | Amount [phr] Rubber mixture II comprising Inv. Example 2 |
|---|---|---|
| 1st stage | | |
| NR TSR$^a$ | 10 | 10 |
| BR$^b$ | 18 | 18 |
| SSBR$^c$ | 72 | 72 |
| Silica$^d$ | 95 | 95 |
| ZnO | 2.5 | 2.5 |
| Stearic acid | 2.5 | 2.5 |
| TDAE oil | 50 | 50 |
| Antiozonant wax | 2 | 2 |

TABLE 1-continued

| Substance | Amount [phr] Ref. rubber mixture I comprising Comp. Ex. 1 | Amount [phr] Rubber mixture II comprising Inv. Example 2 |
|---|---|---|
| 6PPD$^e$ | 2 | 2 |
| Comp. Example 1 | 12 | — |
| Example 2 | — | 14 |
| 2nd stage Batch Stage 2 | | |
| DPG$^f$ | 2 | 2 |
| CBS$^g$ | 2 | 2 |
| Sulphur | 2 | 2 |

Substances used:
$^a$NR TSR: SIR 20 SED, from Aneka Bumi Pratama (TSR = Technically Specified Rubber; SIR = Standard Indonesian Rubber)
$^b$BR: polybutadiene, Europrene Neocis BR 40, from Polimeri
$^c$SSBR: Sprintan ® SLR-4601, from Styron
$^d$silica: ULTRASIL ® VN3 GR, from Evonik Industries AG
$^e$6PPD: N-(1,3-dimethylbutyl)-N'-phenyl-p-phenylenediamine
$^f$DPG: diphenylguanidine
$^g$CBS: N-cyclohexyl-2-benzothiazolesulphenamide The mixture was produced under customary conditions in two stages in a laboratory kneader for production of rubber mixtures (volume 300 milliliters to 3 liters), by first mixing, in the first mixing stage (base mixing stage), all the constituents apart from the vulcanization system (sulphur and vulcanization-influencing substances) at 145 to 165° C., target temperatures of 152 to 157° C., for 200 to 600 seconds. Addition of the vulcanization system in the second stage (ready-mix stage) produces the finished mixture, with mixing at 90 to 120° C. for 180 to 300 seconds.

The general process for producing rubber mixtures and vulcanizates thereof is described in "Rubber Technology Handbook", W. Hofmann, Hanser Verlag 1994.

The rubber testing is effected by the test methods specified in Table 2.

TABLE 2

| Physical testing | Standard/conditions |
|---|---|
| Moving die rheometer (rotorless vulcameter): Minimum torque (dNm) Torque difference: maximum torque − minimum torque (dNm) | ISO 6502 ASTM D5289-12 |
| Rebound resilience at 23° C. (%) | DIN 53512 |
| Dynamic/mechanical analysis at 55° C. Dynamic storage modulus E' at 0.15% elongation and at 8% elongation (MPa) | ISO 4664-1 |

The mixtures were used to produce test specimens by vulcanization under pressure at 160° C. after t$_{95}$ (measured on a moving die rheometer to ISO 6502/ASTM D5289-12). Table 3 reports the rubber data for the vulcanizates.

TABLE 3

| Substance | Ref. rubber mixture I comprising Comp. Ex. 1 | Rubber mixture II comprising Inv. Ex. 2 |
|---|---|---|
| Raw mixture results: | | |
| Moving die method: minimum torque after 3rd stage [dNm] | 4.4 | 3.5 |
| Moving die method: Torque difference: maximum torque − minimum torque (dNm) after 3rd stage | 12 | 18 |

TABLE 3-continued

| Substance | Ref. rubber mixture I comprising Comp. Ex. 1 | Rubber mixture II comprising Inv. Ex. 2 |
|---|---|---|
| Vulcanizate results: | | |
| Rebound resilience 23° C. [%] | 29 | 26 |
| Dynamic/mechanical analysis at 55° C. E' at 0.15% elongation (MPa) | 10.1 | 16.5 |
| Dynamic/mechanical analysis at 55° C. E' at 8% elongation (MPa) | 6.0 | 7.1 |
| Dynamic/mechanical analysis at 55° C. E' at 8% elongation - E' at 0.15% elongation (MPa) | 4.1 | 9.4 |

Rubber mixture II comprising the inventive urea-containing mercaptosilane from Example 2 shows improved processing characteristics (lower minimum torque after the 3rd mixing stage), increased network density (greater difference of maximum torque—minimum torque), improved wet skid properties (rebound resilience at 23° C.) and increased dynamic stiffness (E' at 0.15% elongation, E' at 8% elongation, and E' at 8% elongation—E' at 0.15% elongation) compared to reference rubber mixture I comprising Comparative Example 1 (urea-containing mercaptosilane) used in isomolar amounts.

What is claimed is:

1. A urea-containing mercaptosilane of formula I

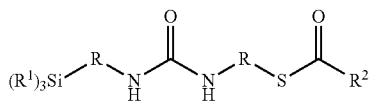

(I)

where each $R^1$ is independently selected from the group consisting of a C1-C10 alkoxy group, a C2-C10 cyclic dialkoxy group, a phenoxy group, a C4-C10 cycloalkoxy group, a C6-C20 aryl group, a C1-C10 alkyl group, a C2-C20 alkenyl group, a C7-C20 aralkyl group or a halogen, $R^2$ is a monovalent C1-C20 hydrocarbon group and each R is independently a branched or unbranched, saturated or unsaturated, aliphatic, aromatic or mixed aliphatic/aromatic divalent C1-C30 hydrocarbon group.

2. The urea-containing mercaptosilane according to claim 1, wherein the urea-containing mercaptosilane is $(CH_3CH_2O)_3Si$—$CH_2$—NH—CO—NH—$CH_2$—S—C(O)—$CH_3$,
$(CH_3CH_2O)_3Si$—$CH_2CH_2$—NH—CO—NH—$CH_2$—S—C(O)—$CH_3$,
$(CH_3CH_2O)_3Si$—$CH_2$—NH—CO—NH—$CH_2CH_2$—S—C(O)—$CH_3$,
$(CH_3CH_2O)_3Si$—$CH_2CH_2$—NH—CO—NH—$CH_2CH_2$—S—C(O)—$CH_3$,
$(CH_3CH_2O)_3Si$—$CH_2CH_2CH_2$—NH—CO—NH—$CH_2$—S—C(O)—$CH_3$,
$(CH_3CH_2O)_3Si$—$CH_2CH_2CH_2$—NH—CO—NH—$CH_2CH_2$—S—C(O)—$CH_3$,
$(CH_3CH_2O)_3Si$—$CH_2$—NH—CO—NH—$CH_2CH_2CH_2$—S—C(O)—$CH_3$,
$(CH_3CH_2O)_3Si$—$CH_2CH_2$—NH—CO—NH—$CH_2CH_2CH_2$—S—C(O)—$CH_3$,
$(CH_3CH_2O)_3Si$—$CH_2CH_2CH_2$—NH—CO—NH—$CH_2CH_2CH_2$—S—C(O)—$CH_3$,
$(CH_3CH_2O)_3Si$—$CH_2$—NH—CO—NH—$CH_2$—S—C(O)—$(CH_2)_6CH_3$,
$(CH_3CH_2O)_3Si$—$CH_2CH_2$—NH—CO—NH—$CH_2$—S—C(O)—$(CH_2)_6CH_3$,
$(CH_3CH_2O)_3Si$—$CH_2$—NH—CO—NH—$CH_2CH_2$—S—C(O)—$(CH_2)_6CH_3$,
$(CH_3CH_2O)_3Si$—$CH_2CH_2$—NH—CO—NH—$CH_2CH_2$—S—C(O)—$(CH_2)_6CH_3$,
$(CH_3CH_2O)_3Si$—$CH_2CH_2CH_2$—NH—CO—NH—$CH_2$—S—C(O)—$(CH_2)_6CH_3$,
$(CH_3CH_2O)_3Si$—$CH_2CH_2CH_2$—NH—CO—NH—$CH_2CH_2$—S—C(O)—$(CH_2)_6CH_3$,
$(CH_3CH_2O)_3Si$—$CH_2$—NH—CO—NH—$CH_2CH_2CH_2$—S—C(O)—$(CH_2)_6CH_3$,
$(CH_3CH_2O)_3Si$—$CH_2CH_2$—NH—CO—NH—$CH_2CH_2CH_2$—S—C(O)—$(CH_2)_6CH_3$ or
$(CH_3CH_2O)_3Si$—$CH_2CH_2CH_2$—NH—CO—NH—$CH_2CH_2CH_2$—S—C(O)—$(CH_2)_6CH_3$.

3. The urea-containing mercaptosilane according to claim 1, wherein the urea-containing mercaptosilane is
$(EtO)_3Si$—$CH_2CH_2CH_2$—NH—CO—NH—$CH_2CH_2$—S—C(O)—$CH_3$.

4. A process for preparing the urea-containing mercaptosilane of claim 1, comprising reacting in an alcohol a halosilane of formula II

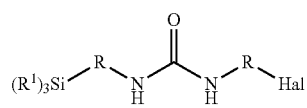

(II)

with a compound of formula III

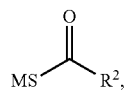

(III)

where $R^1$, $R^2$ and R are each as defined in claim 1, Hal is F, Cl, Br or I and M is an alkali metal.

5. The process of claim 4, wherein the reaction is conducted under a protective gas atmosphere.

6. The process of claim 4, wherein the reaction is conducted at temperatures between 0° C. and 150° C.

7. The process of claim 4, wherein the alcohol is ethanol.

8. The process of claim 4, wherein the halosilane of formula II is prepared by adding a base to a hydrochloride salt of an amine of formula IV

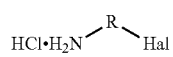

(IV)

and an isocyanatosilane of formula V

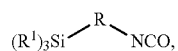

(V)

where Hal, $R^1$ and R are each as defined in claim 4.

9. The process of claim 8, wherein the base is NaOEt.

10. The process of claim 4, wherein the halosilane of formula II is prepared from an isocyanate-halogen compound of formula VI

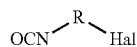

(VI)

and an aminosilane of formula VII

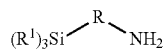

(VII)

where Hal, R and $R^1$ are each as defined in claim 4.

11. The process of claim 10, wherein the reaction is conducted in ethanol.

12. The process of claim 4, wherein the ethanol is distilled off.

13. The process of Process for preparing urea-containing mercaptosilane of the formula I according to claim 12, wherein a product obtained from the reaction is dried.

* * * * *